United States Patent [19]

Gupta et al.

[11] Patent Number: 5,236,841
[45] Date of Patent: Aug. 17, 1993

[54] METHOD FOR REPRODUCING CONIFERS BY SOMATIC EMBRYOGENESIS USING STEPWISE HORMONE ADJUSTMENT

[76] Inventors: Pramod K. Gupta, 32632 26th Ave. S.W., Federal Way, Wash. 98023; Gerald S. Pullman, 16815 - 160th Court S. E., Renton, Wash. 98058

[21] Appl. No.: 705,681

[22] Filed: May 24, 1991

Related U.S. Application Data

[63] Continuation-in-part of Ser. No. 499,151, Mar. 26, 1990, Pat. No. 5,036,007, which is a continuation-in-part of Ser. No. 321,035, Mar. 9, 1989, Pat. No. 4,957,866, and a continuation-in-part of Ser. No. 426,331, Oct. 23, 1989, Pat. No. 5,034,326.

[51] Int. Cl.$^5$ .................... A01H 4/00; A01H 7/00; C12N 5/04
[52] U.S. Cl. .................... 435/240.45; 435/240.4; 435/240.48; 435/240.49; 435/240.54; 800/200; 800/DIG. 49; 800/DIG. 50; 800/DIG. 51; 47/58
[58] Field of Search .......... 435/240.4, 240.45, 240.48, 435/240.54, 240.49; 47/58, DIG. 1, 58.03, 58.05; 800/200, DIG. 47, 48, 49, 50, 51

[56] References Cited

U.S. PATENT DOCUMENTS

| | | | |
|---|---|---|---|
| 4,217,730 | 8/1980 | El-Nil | 47/58 |
| 4,957,866 | 9/1990 | Gupta et al. | 435/240.4 |
| 5,034,326 | 7/1991 | Pullman et al. | 435/240.4 |
| 5,036,007 | 7/1991 | Gupta et al. | 435/240.45 |
| 5,041,382 | 8/1991 | Gupta et al. | 435/240.45 |

OTHER PUBLICATIONS

Gupta et al. (1987) Biotechnology vol. 5, Jul. pp.-710-712.
Becwar, M. R. and R. P. Feirer 1989 Factors regulating loblolly pine (*Pinus taeda* L.) somatic embryo development. *Institute of Paper Chemistry Report*, Southern Forest Tree Improvement Conference, Raleigh, N.C. Jun. 1989 pp. 178-185.
Becwar, M. R., R. Nagmani, and S. R. Wann 1990 Initiation of embryogenic cultures and somatic embryo development in lobloly pine (*Pinus taeda*). *Canadian Journal of Forest Research* 20: 810-817.
Becwar, M. R., T. L. Noland, and S. R. Wann 1987 A method for quantification of the level of somatic embryogenesis among Norway spruce callus lines. *Plant Cell Reports* 6:35-38.
Becwar, M. R., S. R. Wann, and R. Nagmani 1988 A survey of initiation frequency of embryogenic callus among ten families of *Pinus taeda* (loblolly pine). Abstracts, 4th International Conifer Tissue Culture Work Group, Aug. 8-12, 1988, Saskatoon, Saskatchewan, Canada.
Boulay, M. P., P. K. Gupta, P. Krogstrup, and D. J. Durzan 1988 Development of somatic embryos from cell suspension cultures of Norway spruce (*Picea abies* Karst.). *Plant Cell Reports* 7:134-137.

(List continued on next page.)

*Primary Examiner*—Gary Benzion

[57] ABSTRACT

The invention is a method for reproducing coniferous trees by somatic embryo-genesis using plant tissue culture techniques in a multistage culturing process. A suitable explant, typically the fertilized embryo excised from an immature seed, is first cultured on a medium that induces multiple early stage proembryos. These are multiplied in a second culture having reduced growth hormones. The early stage embryos may then be placed in or on a late stage proembryo development culture with a significantly higher osmotic potential than the previous stage or stages in order to develop very robust late stage proembryos having at least 100 cells. Culturing from this point continues in a cotyledonary embryo development medium having a raised osmotic potential. Exogenous abscisic acid is now required at this stage. The concentration of abscisic acid is decreased over time to low levels either by the use of an adsorbent such as activated charcoal or by stepwise subcultures in which the later cultures have lower ABA concentration. After a period of several weeks somatic embryos having the appearance of zygotic embryos will have formed. These may be germinated before or after storage and transplanted to soil for further growth.

18 Claims, 5 Drawing Sheets

OTHER PUBLICATIONS

Bourgkard, F. and J. M. Favre 1988 Somatic embryos from callus of *Sequoia sempervirens.* Plant Cell Reports 7:445–448.

Buchheim, Julie A., Susan M. Colburn, and Jerome P. Ranch 1989 Maturation of soybean somatic embryos and the transition to plantlet growth. *Plant Physiology* 89:768–775.

Durzan, D. J. and P. K. Gupta 1987 Somatic embryogenesis and polyembryogenesis in Douglas-fir cell suspension cultures. *Plant Science* 52: 229–235.

Finer, John J., Howard B. Kriebel, and Michael R. Becwar 1989 Initiation of embryogenic callus and suspension cultures of eastern white pine (*Pinus strobus* L.). *Plant Cell Reports* 8:203–206.

Gupta, Pramod K. and Don J. Durzan 1985 Shoot multiplication from mature trees of Douglas-fir (*Pseudotsuga menziesii*) and sugar pine (*Pinus lambertiana*). Plant Cell Reports 4:177–179.

Gupta, Pramod K. and Don J. Durzan (cont.) 1986a Somatic polyembryogenesis from callus of mature sugar pine embryos. *Bio/Technology* 4:643–645.

1986b Plantlet regeneration via somatic embryogenesis from subcultured callus of mature embryos of *Picea abies* (Norway spruce). *In Vitro Cellular and Developmental Biology* 22:685–688.

1987 Biotechnology of somatic polyembryogenesis and plantlet regeneration in loblolly pine. *Bio/Technology* 5:147–151.

Hakman, Inger and Saravon Arnold 1985 Plantlet regeneration through somatic embryo-genesis in *Picea abies* (Norway spruce). *Journal of Plant Physiology* 121:149–158.

1988 Somatic embryogenesis and plant regeneration from suspension cultures of *Picea glauca* (white spruce). *Physiologia Plantarum* 72:579–587.

Hakman, Inger, L. C. Fowke, S. von Arnold, and T. Eriksson 1985 The development of somatic embryos in tissue cultures initiated from immature embryos of *Picea abies* (Norway spruce). *Plant Science* 38:33–35.

Johansson, Lars 1983 Effects of activated charcoal in another cultures. *Physiologia Plantarum* 59:397–403.

Johansson, Lars, Barbro Andersson, and Tage Eriksson 1982 Improvement of anther culture technique: activated charcoal bound in agar medium in combination with liquid medium and elevated $CO_2$ concentration. *Physiologia Plantarum* 54:24–30.

Lu, Chen-Yi, and Trevor A. Thorpe 1987 Somatic embryogenesis and plantlet regeneration in cultured immature embryos of *Picea glauca.* Journal of Plant Physiology 128:297–302.

Murashige, Toshio and Folke Skoog 1962 A revised medium for rapid growth and bioassays with tobacco tissue cultures. *Physiologia Plantarum* 15:473–493.

Nagmani, R. and J. M. Bonga. 1985 Embryogenesis in subcultured callus of *Larix decidua. Canadian Journal of Forest Research* 15:1088–1091.

Nagmani, R. and M. R. Becwar 1988 Factors affecting somatic embryo development in loblolly pine. *Abstracts*, 4th International Conifer Tissue Culture Work Group, Aug. 8–12, 1988, Saskatoon Saskatchewan, Canada.

Raghavan, V. N. 1986 *Experimental Embryogenesis*, p. 100, McMillan, New York.

Schuller, Astrid and Gerhard Reuther 1989 Response of *Abies alba* embryonal-suspensor mass to various carbohydrate treatments. *Somatic Cell Genetics Working Party* S2-04-07 and *NATO Advanced Research Workshop on Woody Plant Biology*, Institute of Forest Genetics, Placerville, California, Oct. 15-19, 1989 (Abstract).

Singh, Hardev 1978 "Embryo" in *Embryology of Gymnosperms*, Chapter 11, Gebruder Borntrager, Berlin.

Teasdale, Robert D., Pamela A. Dawson, and H. W. Woolhouse. 1986 Mineral nutrient requirements of a loblolly pine (*Pinus taeda*) cell suspension culture. *Plant Physiology* 82:942–945.

Verhagen, S. and S. R. Wann 1989 Norway spruce somatic embryogenesis: high frequency initiation from light colored mature embryos. *Plant Cell Tissue and Organ Culture* 16:103–111.

Von Arnold, Sara 1987 Improved efficiency of somatic embryogenesis in mature embryos of *Picea abies* (L.) Karst. *Journal of Plant Physiology* 128:233–244.

Von Arnold, Sara and Inger Hakman 1988 Regulation of somatic embryo development in *Picea abies* by abscisic acid (ABA). *Journal of Plant Physiology* 132:164–169.

Yeung, Edward C. and D. C. W. Brown 1982 The osmotic environment of developing embryos of *Phaseolus vulgaris. Z. Pfanzenphysiol. Bd.* 106 S.:149–156.

Ziv, Meira and Geula Gadasi 1986 Enhanced embryogenesis and plant regeneration from cucumber (*Cucumis sativus* L.) callus by activated charcoal in solid/liquid double-layer cultures. *Plant Science* 47:115–122.

METHOD FOR REPRODUCING CONIFERS BY SOMATIC EMBRYOGENESIS USING STEPWISE HORMONE ADJUSTMENT

This application is a continuation-in-part of our earlier application Ser. No. 449,151, filed Mar. 26, 1990, and now U.S. Pat. No. 5,036,007, which was a continuation-in-part of applications Ser. No. 321,035, filed Mar. 9, 1989, now U.S. Pat. No. 4,957,866, and Ser. No. 426,331, filed Oct. 23, 1989, now U.S. Pat. No. 5,034,326.

BACKGROUND OF THE INVENTION

The present invention is a method for reproducing coniferous plants by somatic embryogenesis using the techniques of plant tissue culture. It is especially suited for producing large clones of superior selections useful for reforestation.

Loblolly pine (*Pinus taeda* L.), its closely related southern pines, and Douglas-fir (*Pseudotsuga menziesii* (Mirb.) Franco) are probably the most important commercial species of temperate North American timber trees. Similarly, Norway spruce (*Picea abies* (L.) Karst.) is probably the most important European softwood species. Since the early 1940s, when serious private reforestation efforts began, literally billions of one and two year old nursery-grown trees have been planted on cutover or burned forest lands. For many years these seedling trees were grown using naturally produced seed from cones collected as a part time effort of individuals seeking to supplement their incomes. As early as 1957 forest geneticists began to plant seed orchards using either seed or grafted scions obtained from superior trees discovered in the forests. These trees were selected for such inheritable characteristics as rapid growth, straightness of bole, wood density, etc. Now in both the southern pine and Douglas-fir regions the bulk of the seed is produced from selected trees grown in seed orchards, some of them now second and third generation orchards.

Despite the fact that the orchards were stocked with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominately angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

Culture by organogenesis is tedious and expensive due to the large amount of delicate manual handling necessary. It was soon recognized that embryogenesis was potentially a much more desirable method from the standpoints of quantity of plantlets produced, cost, and potential genetic gain. Work on embryogenesis of forest species began in the late 1970s. U.S. Pat. No. 4,217,730 to El-Nil describes one early attempt at somatic embryogenesis of Douglas-fir. This approach was later set aside because advanced stage embryos and plantlets could not be readily obtained. However, other workers entered the field in increasing numbers and progress has been rapid even if it has not until the present time reached the commercial stage. A brief review of some of the most important work will follow. This is intended to be representative and is not fully inclusive of all the work in the field. Literature citations in the text are given in abbreviated form. Reference should be made to the bibliography at the end of the specification for full citations of the literature noted herein.

The natural embryogeny of gymnosperms is described in great detail by Singh (1978). Conifer-type embryogeny is one of four types noted for gymnosperms. This includes virtually all of the important forest species except Sequoia. Singh notes that the immature seeds typically contain more than one embryo. Most commonly this seems to occur when a single zygote forms multiple embryos, a phenomenon called "cleavage polyembryony". As the seed matures one embryo becomes dominant while the others are suppressed. The ability to form multiple embryos from a single zygote forms the basis for most of the present embryogenic processes for multiplying conifers. However, Douglas-fir is an exception. Most typically only a single embryo will be present throughout the formation and maturation of a seed. This may account for at least some of the difficulty experienced to date in multiplying Douglas-fir by somatic embryogenesis.

Bourgkard and Favre (1988) describe what is the apparently successful production of plantlets by somatic embryogenesis of *Sequoia sempervirens*. As a historic note, this was one of the first forest tree species successfully reproduced by organogenesis.

Hakman and her coworkers have concentrated on Norway spruce (*Picea abies*), apparently with some success. In a paper by Hakman, Fowke, von Arnold, and Eriksson (1985) the authors describe the production of "embryos" but not plantlets. Hakman and von Arnold (1985) do suggest that they have successfully obtained plantlets. This latter paper is interesting for its comments on the variability within the species and the poor success with many of the seed sources used for explants. The authors suggest that this variability may be due to the physiological condition of the source material. However, other workers have noted great differences in behavior between recognized genotypes of the species.

Nagmani and Bonga (1985) describe embryogenesis from megagametophytes of *Larix decidua* by tissue culture. The archegonia, proembryos, or embryos with their suspensors were removed prior to culture. Some of the resulting embryos produced in culture were stated to have further advanced to become plantlets established in soil. The ploidy of these plants was not investigated.

Successful production of small quantities of plantlets has now been reported for loblolly pine. Teasdale, Dawson, and Woolhouse (1986) showed the criticality of proper mineral nutrients for cell suspension cultures of loblolly pine. The article by Becwar, Wann, and Nagmani (1988) is enlightening for the differences shown in performance between different families (or genotypes). Three families out of the ten tried accounted for most of their success. Even so, they appeared unable to grow cotyledonary embryos. A companion paper by Nagmani and Becwar (1988) showed development of *Pinus taeda* to the precotyledonary stage. In an earlier paper, Gupta and Durzan (1987) described their success in taking loblolly pine to the plantlet stage by embryogenesis. However, only one genotype was successfully taken to the plantlet stage and only one converted plant was produced. The authors note the need for "improved conversion rates" as well as other information before the process can be considered commercially practical.

Sugar pine (*Pinus lambertiana*) has also been cultured to the plantlet stage as reported by Gupta and Durzan (1986a). The authors note a very low 1-2% conversion of embryos into plantlets.

The researchers just noted appear to be the only others who have previously achieved success in producing Douglas-fir plantlets by embryogenesis (Durzan and Gupta 1987). Again, the success ratio appears to be very low and they have obtained only two converted plants from a single genotype.

In our earlier application, Ser. No. 321,035, filed Mar. 9, 1989, now U.S. Pat. No. 4,957,866, which is a grandparent to the present application, we described an improved method for reproducing coniferous species by somatic embryogenesis. An intermediate high osmoticant culture medium was used to generate strong late stage proembryos. This was done prior to the development of cotyledonary embryos in a medium containing abscisic acid. The methods disclosed were of particular effectiveness in somatic polyembryogenesis of loblolly pine. In Ser. No. 426,331, filed Oct. 23, 1989, Now U.S. Pat. No. 5,034,326, the other grandparent application to the present one, we disclosed the use of a combination of abscisic acid with activated charcoal in a cotyledonary embryo development medium. The charcoal is believed to gradually reduce the concentration of abscisic acid during the development period. This improvement resulted in the production of more robust embryos with a much reduced tendency for precocious germination.

Activated charcoal has been widely used before in tissue culture media where it is believed to function as an adsorbent for toxic metabolic products and undesirable amounts of residual hormones. Abscisic acid has also been recognized as being a useful plant hormone in cultures inducing conifer embryogenesis; e.g., Boulay, Gupta, Krogstrup, and Durzan (1988). The combination of these two materials has been used by a number of workers, generally with indifferent or negative results. Johansson, Andersson, and Ericksson (1982) cultured anthers of several ornamental plant species using a two phase liquid over solid medium in which the agarified solid phase contained activated charcoal. The charcoal appeared to be useful for absorbing small amounts of endogenous abscisic acid. In a related paper, Johansson (1983) tested the effects of charcoal as an adsorbent of materials inhibiting the initiation of embryogenesis. In a test intended as a model, he added exogenous ABA in amounts varying by orders of magnitude between $10^{-9}M$ and $10^{-3}M$ to media with and without activated charcoal in the solid portion of a two phase medium. His conclusion was that initiation was completely inhibited for all of the test species at ABA concentrations above $10^{-6}M$, when no charcoal was used, and $10^{-4}M$ when charcoal was present. Thus, charcoal was seen as an effective material for removing inhibitory amounts of ABA and other undesirable materials such as phenolics.

Ziv and Gadasi (1986) studied embryogenesis in several genotypes of cucumber (*Cucumis sativus* L.). They used liquid cultures as well as the two layer technique with activated charcoal in the solid layer of the medium and low (0.4 $\mu M$) levels of abscisic acid in the liquid layer. In the liquid cultures abscisic acid by itself only slightly improved embryo formation and was significantly more effective than the combination of abscisic acid with activated charcoal. Plantlet development in the liquid over solid cultures was slightly improved by the combination of the two materials.

Buchheim, Colburn, and Ranch (1989) suggest that exogenous abscisic acid and activated charcoal would probably not be a very useful combination of ingredients in a culture medium because of adsorption of the abscisic acid by the charcoal with subsequent loss of its biological effectiveness.

Since the importance of the osmotic environment within a developing seed is known (Yeung and Brown 1982), it has been assumed by others that the osmotic potential of the media during a culturing process could have an important effect (e.g., Raghavan 1986). Lu and Thorpe (1987), using white spruce (*Picea glauca*), noted that increasing the osmolality of a medium and reducing the auxin concentration enhanced development and maturation of somatic embryos. They observed that more embryos developed on media containing 6% than on those with 9% sucrose and that similar results were obtained when sorbitol replaced 3% of the sucrose in the medium. Sorbitol is known to be only poorly metabolized so presumably its effect was osmotic rather than as a carbon source for the developing embryos. Quite in contrast to their findings, Hakman and von Arnold (1988), using the same species and a combination of abscisic acid and sucrose in a development medium, found a very sharp falloff in success in going from 3% to 4% sucrose.

Becwar and Feirer (1989) note work involving the transfer of a loblolly pine embryonal-suspensor mass to development media containing 10 $\mu M$ abscisic acid with 3-6% sucrose. However, they reported no details of their experimental protocol and only that the media "promoted embryo development". A later paper by Becwar, Nagmani, and Wann (1990) gives further details of initiation of the cultures and describes hormone requirements and the effect of embryo maturity for 10 full sib families.

Finer, Kreibel and Becwar (1989), studying eastern white pine (*Pinus strobus* L.), initiated and maintained cultures on media with a 3% sucrose level. Further embryo development was then attempted on a medium with 1-12% sucrose combined with a high concentration of abscisic acid and varying amounts of glutamine. Best results were found with 50 mM glutamine, 38 $\mu M$ abscisic acid, and 6% sucrose. However, the number of embryos formed under any of the conditions was not high and, as of the time of reporting, none has been successfully germinated and converted into plants.

Schuller and Reuther (1989), in the abstract of a paper, describe the study of several sugars and soluble starch as carbohydrate sources for the culture of *Abies alba*. They note that development was obtained only on a medium using soluble starch and lactose. No details were given and apparently no somatic embryos were developed to the cotyledonary stage.

Von Arnold (1987) investigated carbohydrate level of the initiation medium for Norway spruce. Sucrose was varied between about 1–3% with successful initiation being obtained at the higher level on half strength medium. By replacing a portion of the sucrose with sorbitol she showed that the poorer results on full strength medium were not due to increased osmotic pressure.

Von Arnold and Hakman (1988) took a Norway spruce embryogenic callus and transferred it to a modified intermediate medium prior to full embryo development. The intermediate medium contained abscisic acid and from 1–3% sucrose. The higher sucrose levels, along with the abscisic acid, resulted in increased frequency of advanced stage proembryo development.

The potential for achieving genetic gain using somatic embryogenesis is recognized as being very great. However, the problems to date have been so overwhelming that commercial application has seemed reasonably close at hand only for Norway spruce and, to a lesser extent, loblolly pine and Douglas-fir using the methods described in our parent applications. Possible large scale commercial production of replanting stock by embryogenesis has remained no more than a fond hope in the minds of the people working in the field.

BRIEF DESCRIPTION OF THE DRAWINGS

The figures show various stages of plant embryogenesis in which.

SUMMARY OF THE INVENTION

The present invention is a method of reproducing selected plants by somatic embryogenesis using tissue culture techniques. It is particularly concerned with control of exogenous hormone level in the cotyledonary embryo development stage of culture. More particularly, the invention relates to the use of gradually decreasing amounts of the plant hormone abscisic acid during the time when proembryos are further developed into cotyledonary embryos. The method is especially suitable for reproducing woody gymnosperms of the order Coniferales. It is particularly well suited for generating large clones of superior forest trees for reforestation, including species within the families Pinaceae, Cupressaceae, and Taxodiaceae. Most or all species within the genera Abies, Pinus, Picea, Tsuga, Pseudotsuga, Thuja, Juniperis, Larix, Taxus and Sequoia are believed to be amenable to multiplication by the present method.

The method is particularly advantageous in that it enables greater quantities and more robust somatic embryos to be produced. This results in higher numbers of embryos that can be successfully converted into plants growing in soil. Costs per plant can be significantly reduced over prior known tissue culture methods. In addition, use of the method generates embryos that can be retained for extended periods of time in cryogenic storage or, alternatively, in cold storage without the need to transfer them from a development medium.

A number of terms are known to have differing meanings when used in the literature. The following definitions are believed to be the ones most generally used in the field of botany and are consistent with the usage of the terms in the present specification.

"Auxins" are plant growth hormones that promote cell division and growth.

"Cytokinins" are plant growth hormones that affect the organization of dividing cells.

"Callus" is generally considered to be a growth of unorganized and either unconnected or loosely connected plant cells generally produced from culturing an explant.

"Embryogenic callus" is a translucent white mucilaginous mass that contains early stage proembryos attached to suspensors. This is also referred to as an "embryonal-suspensor mass" or "ESM" by some investigators.

A "proembryo" is a cell or group of cells having the potential to become a plant but lacking defined meristematic organ primordia.

Figure 1:
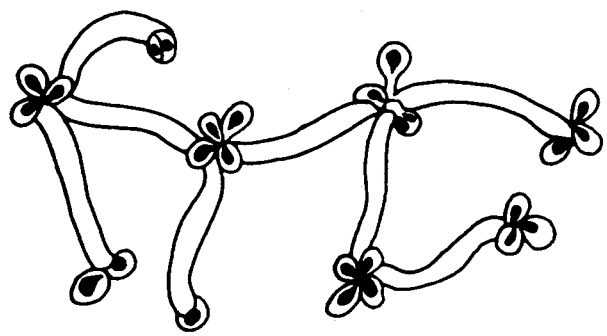
FIG. 1 shows early stage proembryos.

An "early stage proembryo" is a mass generally of 1–10 cells with dense cytoplasm and large nuclei that have the potential of forming a plant. The early stage proembryo is normally found as a head associated at the end of a long thin-walled suspensor cell (FIG. 1).

Figure 2:
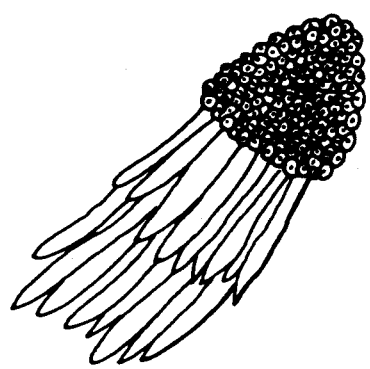
FIG. 2 shows late stage proembryos.

A "late stage proembryo" is a proembryo with a smooth embryonal head of at least about 100 cells associated with multiple suspensor cells. The late stage proembryo is a very robust advanced proembryo (FIG. 2).

Figure 3:
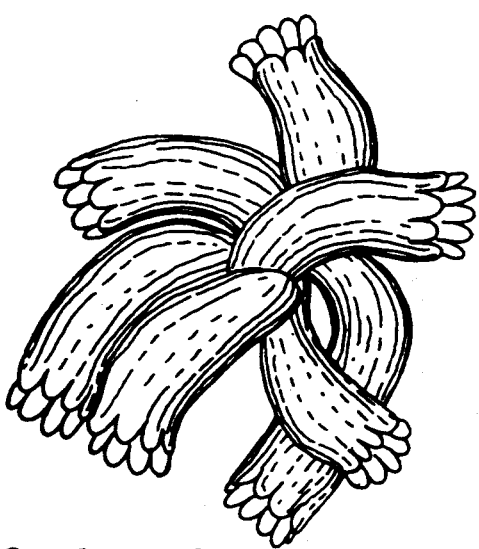
FIG. 3 depicts cotyledonary stage embryos.
Figure 9:
FIG. 9 is a photomicrograph of high quality Douglas-fir cotyledonary embryos.

A "cotyledonary embryo", sometimes simply referred to as an "embryo", has a well defined elongated bipolar structure with latent meristematic centers having cotyledonary primordia at one end and a potential radicle at the opposite end. The cotyledonary structure frequently appears as a small "crown" at one end of the embryo (FIGS. 3 and 9). A cotyledonary somatic embryo is analogous to a developed zygotic embryo.

An "explant" is a piece of tissue taken from a donor plant for culturing.

A "meristem" or "meristematic center" is a group of tissue forming cells capable of further development into plant organs; e.g., shoots and roots.

An "osmoticant" or "osmoticum" is a chemical material used for controlling the osmotic potential of a solution. In the present context the solution would be a culture medium.

Figure 4:
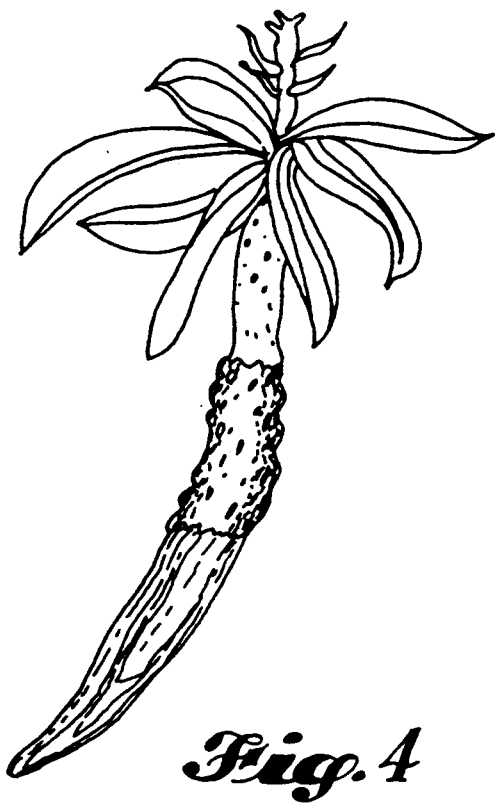
FIG. 4 shows a plantlet ready for transfer to soil.

A "plantlet" is a plant asexually reproduced by tissue culture (FIG. 4).

A "converted embryo" is an embryo that has germinated and been established as a plant growing in soil "Somatic embryogenesis" is the process using tissue culture techniques for generating multiple embryos from an explant. The embryos from a given tissue source are presumed to be genetically identical.

The present method as a whole comprises a multistage culturing process. A suitable explant is first placed on an induction or initiation culture medium. This usually will contain relatively high quantities of growth hormones including at least one auxin and frequently one or more cytokinins. However, growth hormones at this initial stage are not always necessary or desirable for induction of early stage proembryos. A number of sources of explants may ultimately prove to be satisfactory for culturing. These include, but are not limited to, tissue from cotyledons, hypocotyls, epicotyls, buds, meristematic centers for buds or roots, and seed embryos. Zygotic embryos removed from seeds are presently preferred. In particular, for species which in the past have proved to be very difficult or impossible to propagate by somatic embryogenesis, the embryos from immature seeds may be preferred. In the case of Douglas-fir, an embryo selected between the time that an apical dome begins to form but before the first appearance of cotyledon primordia appears to be optimum.

The first stage or induction medium will normally be one of those well known from past work which contain a balanced concentration of inorganic salts and organic nutrient materials, with plant growth hormones included as noted above. Auxins are normally present in concentrations which may initially be as high as about 600 $\mu$M/L, more typically not exceeding about 500 $\mu$M/L. Cytokinins, if present, may initially be as high as 500 $\mu$M/L. The plant growth hormones may include at least one auxin and one cytokinin in a combined initial concentration not exceeding about 1100 $\mu$M/L, more typically not exceeding about 900 $\mu$M/L. The particular auxins and cytokinins used and their exact concentrations, or whether they are used at all, will depend somewhat on the species being cultured and even on the particular genotype within that species. This is something that cannot be easily predicted but can be readily determined experimentally. These very high levels of growth hormones assume the presence in the medium of an adsorbent material, such as activated charcoal. Where charcoal is not present the levels of growth hormones would normally be much lower; e.g., a full order of magnitude, than those just noted.

Culturing during this stage may be carried out in the dark, under very low light conditions, or in full light until an embryogenic mass forms. Lighting conditions will depend in large part on the composition of the particular medium selected. This embryogenic mass has been described by various other names by researchers who have reported it in the past; e.g., embryogenic callus (Hakman and von Arnold 1985) or embryonal-suspensor mass (Durzan and Gupta 1987). It has the appearance of a whitish, translucent, mucilaginous mass containing early stage proembryos which are readily apparent by low power light microscopy. In the case of Douglas-fir the presence of activated charcoal or a similar adsorbent in the initiation medium appears to be quite advantageous. It was noted earlier that Douglas-fir does not experience polyembryony as do most other coniferous species. The reasons for this are not well understood but one hypothesis suggests that Douglas-fir seeds contain a high endogenous level of abscisic acid which suppresses polyembryony. Activated charcoal in the initiation medium may remove this endogenous ABA, as well as other undesirable metabolic by-products, to allow polyembryony to occur in vitro. Because the charcoal will also gradually remove growth hormones over time the initial concentrations of these materials are necessarily higher than might otherwise be the case. The preferred induction medium for Douglas-fir will preferably contain an auxin or auxins in amounts of about 400-600 $\mu$M/L and a cytokinin or cytokinins in the amount of about 240-500 $\mu$M/L.

Early stage proembryos from the first culture may be directly transferred to a late proembryo development culture medium having significantly reduced plant growth hormones and, for some species, a higher concentration of osmoticants. However, they are preferably first subcultured in a maintenance medium of similar or slightly higher osmotic potential than the induction medium for multiplication. This multiplication medium will also usually have the concentration of plant hormones significantly reduced below that of the induction medium. By "significantly reduced" is meant lowered by a factor which may typically be one whole order of magnitude. In the case of Douglas-fir it may be two full orders of magnitude below that initially present in the induction medium. No hormone adsorbent is usually necessary or desirable at this time. The osmotic potential of the induction and maintenance medium will most often not exceed about 160 mM/kg.

The composition and use of the late proembryo development culture medium is important to the success of the present process. It differs from the induction medium by having a similar level of plant growth hormones to those present in the maintenance and multiplication medium. However, for many species such as *Pinus taeda* and *Pseudotsuga menziesii*, the late proembryo development media should have a concentration of osmoticants that is significantly raised above that of the induction or multiplication media. The optimum osmoticant levels at each stage will usually differ for each species and often for individual genotypes within a species. For loblolly pine the osmotic level should typically be of the magnitude of at least 200 mM/kg and preferably about 240 mM/kg or even higher. However, lower levels of about 170 mM/kg minimum will suffice for most genotypes of Douglas-fir. The key advantage of this osmotic "pulse" is that proembryo quality and/or size can be significantly improved. Some species such as *Picea abies*, which are relatively easy to reproduce, may not require this raised osmotic level, or it may only be necessary for some genotypes. In these cases late proembryo development may usually be achieved without a change in medium composition from the maintenance and multiplication medium.

Incubation at this stage is usually carried out in the dark or in greatly reduced light until robust late stage proembryos have formed. These may then be transferred to an embryo development medium which preferably lacks auxins and cytokinins entirely.

Many investigators refer to cotyledonary embryo development from proembryos simply as a "development" stage and that usage will be understood herein unless the word "development" is otherwise qualified.

Figure 7:
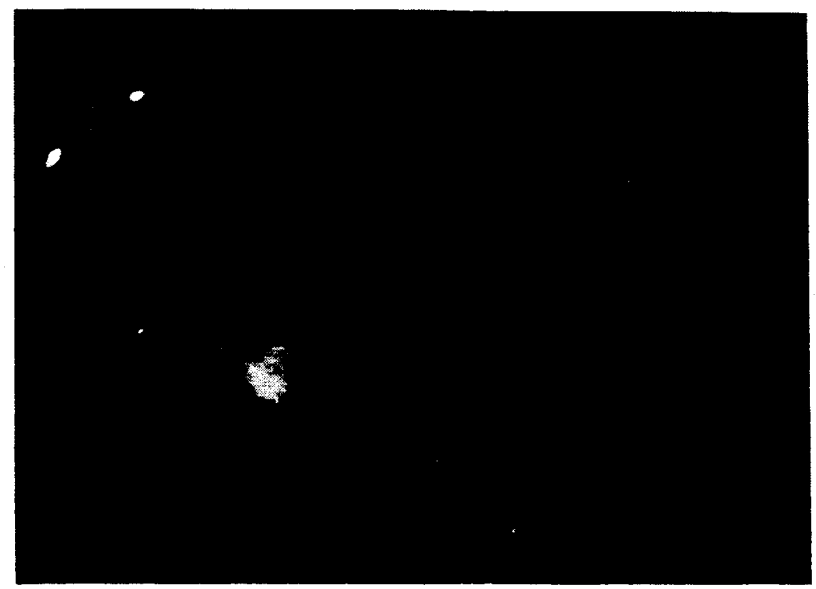
FIG. 7 is a photomicrograph of embryos after singulation.
Figure 8:
FIG. 8 is a photomicrograph of a clump of unsingulated Douglas-fir cotyledonary embryos.

Douglas-fir generally requires an intermediate step between the late proembryo growth stage and the final cotyledonary embryo development stage which is not necessary for other species. The proembryos tend to form in tight clumps or clusters (FIG. 6) which must first be singulated before going to the development stage. This singulation is carried out in a liquid shake culture which lacks auxins and cytokinins but has exogenous abscisic acid as a necessary new hormone. The level of osmotic potential is also reduced from that of the late stage proembryo development medium. ABA will initially usually be within the range of 5–15 mg/L(20/60 μM/L) with osmotic potential levels in the range of 130–160 mM/kg. It is desirable when transfers to fresh media are made that the initial ABA level of the fresh medium should not be higher than the final level of the medium at the end of the preceding culture period. This will ensure a continuously dropping level of ABA during the singulation period. The singulated late stage proembryos (FIG. 7) can then be transferred to a solid or pad-on-liquid cotyledonary embryo development medium. If the embryos are not singulated they will develop into a tight clump of cotyledonary embryos which cannot be readily separated and are difficult to use for further germination (FIG. 8).

Further embryo development and enlargement will begin to occur during the singulation stage for Douglas-fir. Abscisic acid is preferably reduced in step-wise fashion during the singulation period. By stepwise is meant that a significant reduction in abscisic acid level occurs from stage to stage. This will generally mean that the ABA level in each medium will be reduced to no more than about 50% of that initially present in the previous medium.

Significantly, species other than Douglas-fir can be advantageously cultured by beginning early cotyledonary embryo development in a series of media similar to those used for Douglas-fir singulation. Abscisic acid should be initially present in amounts in the range of about 5–100 mg/L, more preferably about 5–20 mg/L. ABA is gradually reduced in three or four steps to levels no greater than about 0–10 mg/L, more preferably about 0–2.5 mg/L, and most preferably about 0–1 mg/L. The exact levels chosen will depend somewhat on species and genotype.

The singulation stages are preferably carried out in Douglas-fir culture in liquid media under gently agitated conditions. Other species may produce better results if the early development cultures are made on solid medium or on pad systems using liquid medium. However, for all species it is most desirable for a final development stage or stages to be carried out on either solid medium or with liquid medium using a pad system. For reasons not perfectly understood, far more vigorous embryos are normally obtained when they are exposed to air in the final development stages.

Especially when Douglas-fir is being cultured, but also with some genotypes of loblolly pine and other species, the osmotic potential of the later stage cotyledonary development medium should be sharply raised above that of any of the preceding media. Initially levels may be in the 300–350 mM/kg range but these should be increased to levels of at least about 400 mM/kg as development proceeds. If development is started at levels around 300–350 mM/kg, the osmotic level may be increased during development by a complete medium change, a partial change in which some old medium is replaced, or by adding an appropriate form, such as a solution, of osmoticants to the medium without replacement of any of the original medium. Any of these changes may be considered a transfer to a "new" medium. With Douglas-fir, it is preferred that the osmotic levels at the end of the development period should be at least about 450 mM/kg although with some genotypes lower levels are acceptable. With some Douglas-fir genotypes final osmotic levels as high as 600 mM/kg have given superior results. These higher levels tend to prevent deterioration and callusing of the embryos.

Osmotic potential in the later stages of cotyledonary development is best controlled by a combination of osmoticants. One of these should be a readily metabolized carbohydrate energy source, preferably a sugar such as sucrose, glucose, fructose, maltose, or galactose. Sucrose is a preferred ingredient and may be present in amounts in the range of 2–6%. The other is a poorly metabolized osmoticant of which sorbitol, lactose, or a polyalkylene glycol would be examples. In a solid development medium, a combination of sorbitol, lactose and polyethylene glycol has proved very effective. Polyethylene glycol (PEG) alone, in concentrations of 20–30% of the medium, has worked very well in liquid development media. The molecular weight of the PEG is not critical and may fall in the range of several hundred to several thousand. While the salts and organic components of the medium make a small contribution to the osmolality, the osmotic potential is primarily controlled by the energy-providing sugar and the other osmoticants. It is within the scope of the invention to use one combination of osmoticants at the beginning of development and transfer to a medium having a different combination at some point during the development stage.

In some cases where transfers to fresh media are made during the cotyledonary embryo development stage, especially when culturing Douglas-fir, at least the final and most preferably the penultimate media should have osmotic potentials of at least about 350 mM/kg, preferably about 400 mM/kg or higher.

For virtually all coniferous species a supply of exogenous abscisic acid is an essential hormone and media component in the development from proembryos to cotyledonary embryos. As was described in our earlier U.S. Pat. Nos. 5,034,326 and 5,036,007, this was always used at some point in time in combination with an adsorbent, such as activated charcoal. The adsorbent was present in a sufficient amount and form to slowly reduce the abscisic acid and remove metabolic waste products. It could not be present in such a high concentration as to deplete the abscisic acid in a very short time; e.g., in a matter of days. The combination of abscisic acid with the adsorbent usually required a higher initial concentration of abscisic acid than was the case if no adsorbent was present in the medium.

In the particular case of Douglas-fir, but with other species as well, we have found that the level of exogenous abscisic acid should be generally continuously lowered over time from the 5–15 mg/L normally found necessary at the beginning of the singulation step or cotyledonary embryo development stage to a level perhaps of about 1–2 mg/L, or even to zero, at the end of the development stage. Accurate measurements of abscisic acid present in the development stage have not yet been made due to the extreme difficulties of analyzing the medium.

Reduction of abscisic acid and other hormone materials by an adsorbent normally proceeds in an exponential fashion until the full capacity of the adsorbent is reached. This means that the concentration of hormone will initially drop at a high rate and then more slowly over time. This change in abscisic acid concentration is not always optimum and may, in many cases, be better controlled using the methods of the present invention.

We have now discovered that the use of activated charcoal in the embryo development stage is not essential and, in some case, may not even be desirable. The same benefit can be obtained by a gradual reduction, usually in stepwise fashion, of abscisic acid through media transfers. This has a number of benefits. One is that more precise control of abscisic acid level is possible at given points in time during cotyledonary embryo development. The stepwise development cultures may be all on solid phase cultures or their equivalents. Alternatively, initial cultures may be in liquid media and culturing may be completed on solid phase cultures. An absorbent pad system or a liquid medium in which the developing embryos are on a filter paper or similar support on the surface of the medium should be considered as equivalent to a gelled or agarified solid culture. In a "solid phase culture" there is no agitation and the embryos are on the surface where they are exposed to the ambient gases in the culture dish.

In some cases when Douglas-fir is being cultured, sufficient abscisic acid will be carried over with the medium associated with the embryos from the singulation step so that no additional initial exogenous ABA is needed in the final development medium. By "final" is meant the solid or pad-type culture systems noted earlier in which the developing embryos are exposed to air. In other cases, the level of endogenous ABA after singulation is sufficiently high so that no initial exogenous ABA need be present at all at this time. The terms "sufficient" or "having an adequate supply of" should be considered broad enough to encompass either of these situations. Reduction of ABA to low levels at the end of the development stage seems to help continue late embryo development and maturation and also reduces the tendency of precocious germination of the embryos.

Following embryo development the embryos (FIG. 9) may be placed directly on a germination medium for conversion into plantlets. Alternatively, they may be converted into artificial seeds by any of a number of published processes.

An advantage of the present process was the discovery that the more robust somatic embryos produced by the reducing the abscisic acid level during the development period could be readily stored for extended periods of time. Several genotypes of at least two coniferous species (*Pseudotsuga menziesii* and *Picea abies*) have now been stored without loss of vitality for at least seven months at 4°-5° C. without subculturing or otherwise removing them from the development medium. *Pinus taeda* has been stored for over three months. This has not been believed possible with any degree of success before the present invention.

The germination medium has no exogenous hormones, a lowered organic nitrogen content, and a reduced level of osmoticants. After a sufficient time in darkness followed by light, or a 16 hour light and 8 hour dark photoperiod, the cotyledonary embryos will have developed into plantlets. Douglas-fir does not require an initial dark period although an initial four day dark period is usually more satisfactory. A one week dark period is useful for Norway spruce. The time period for germination will be about 1-2 months. The resulting plantlets will have a well developed radicle and cotyledonary structure with a growing epicotyl and are ready for planting in soil.

The present invention is most particularly concerned with the composition of the cotyledonary embryo development media and method of its use. For Douglas-fir in particular, and other conifer species as well, it has been found that a very high osmotic level in combination with a diminishing level of exogenous abscisic acid is highly advantageous. This combination gives greatly improved numbers and quality of somatic embryos that are not subject to precocious germination.

It is an object of the present invention to produce coniferous plantlets by somatic embryogenesis.

It is another object to produce a large clone of a genetically selected forest species for reforestation using the methods of somatic embryogenesis and plant tissue culture.

It is a further object to provide a method of somatic embryogenesis that will dependably and consistently provide coniferous plantlets in large quantities.

It is yet another object to provide a method of somatic embryogenesis that can dependably and consistently reproduce large clones of selected individuals of forest species that heretofore have not been successfully reproduced by this method.

It is still a further object to provide a method whereby superior genotypes of coniferous trees can be multiplied by tissue culture in the large quantities needed for reforestation.

It is also an object to provide a method that will produce somatic embryos in large quantities with improved robust morphology for conversion into plantlets.

It is a particular object to provide a method and suitable culture media for somatic embryogenesis that produces robust somatic embryos with a high percentage of conversion to plants growing in soil.

It still another object to provide a method that generates robust somatic embryos capable of withstanding extended periods of cold storage or cryogenic preservation.

These and many other objects will become readily apparent to those skilled in the art by reading the following detailed description, taken in conjunction with the drawings.

DETAILED DESCRIPTION OF THE PREFERRED EMBODIMENTS

The process of the present invention is not limited to any single culture medium or to the use of specific growth hormones. Any of a number of well known media, such as that of Murashige and Skoog (1962), may be used. However, the present inventors have found the basal medium described in Table 1 to give excellent results, particularly when used for culturing loblolly pine (*Pinus taeda*). The basal medium is modified for each of the various culturing stages as shown in Table 2. Similar media particularly preferred for Norway spruce (*Picea abies*) are given in Tables 4 and 5 and for Douglas-fir in Tables 7 and 8.

TABLE 1

| *Pinus Taeda* Basal Medium (Modified ½ P6 Basal Salts*) | |
|---|---|
| Constituent | Concentration, mg/L |
| NH$_4$NO$_3$ | 603.8 |
| KNO$_3$ | 909.9 |
| KH$_2$PO$_4$ | 136.1 |
| Ca(NO$_3$)$_2$.4H$_2$O | 236.2 |
| MgSO$_4$.7H$_2$O | 246.5 |
| Mg(NO$_3$)$_2$.6H$_2$O | 256.5 |
| MgCl$_2$.6H$_2$O | 50.0 |
| KI | 4.15 |
| H$_3$BO$_3$ | 15.5 |
| MnSO$_4$.H$_2$O | 10.5 |
| ZnSO$_4$.7H$_2$O | 14.4 |
| NaMoO$_4$.2H$_2$O | 0.125 |
| CuSO$_4$.5H$_2$O | 0.125 |
| CoCl$_2$.6H$_2$O | 0.125 |
| FeSO$_4$.7H$_2$O | 6.95 |
| Na$_2$EDTA | 9.33 |

TABLE 1-continued

Pinus Taeda Basal Medium (Modified ¼ P6 Basal Salts*)

| Constituent | Concentration, mg/L |
|---|---|
| Sucrose | 30,000. |
| myo-Inositol | 1,000.0 |
| Casamino acids | 500.0 |
| L-Glutamine | 1000.0 |
| Thiamine.HCl | 1.00 |
| Pyridoxine.HCl | 0.50 |
| Nicotinic acid | 0.50 |
| Glycine | 2.00 |
| Agar+ | 6,000.0 |
| pH adjusted to 5.7 | |

*According to Teasdale, Dawson, and Woolhouse (1986) as modified
+Used if a solid medium is desired

TABLE 2

Composition of Media for Different Stage Treatments $BM_1$ Induction Medium
  BM + 2,4-D (50 μM) + KIN (20 μM) + BAP (20 μM)
$BM_2$ Maintenance and Multiplication Medium
  BM + 2,4-D (5 μM) + KIN (2 μM) + BAP (2 μM)
$BM_3$ Late Proembryo Development Medium
  $BM_2$ + 9000 mg/L myo-inositol
$BM_4$ Embryo Development Medium
  BM + 4.0 to 8.0 mg/L abscisic acid decreasing over time
$BM_5$ Germination Medium
  BM modified by reducing sucrose to 20,000 mg/L, myo-inositol to 100.0 mg/L, glutamine to 200.0 mg/L, and casamino acids to 0.0 mg/L A number of abbreviations are used in the following text. These are in common use in the field of tissue culture.

BAP—$N^6$-benzylaminopurine (or $N^6$-benzyladenine), a cytokinin.
KIN—kinetin (6-furfurylaminopurine), also a cytokinin.
2,4-D—2,4-dichlorophenoxyacetic acid, an auxin.
NAA—2-Naphthylacetic acid (naphthalene-2-acetic acid).
ABA—Abscisic acid (5-(1-hydroxy-2,6,6,-trimethyl-4-oxo-2-cyclohexen-1-yl)-3-methyl-2,4-pentadienoic acid).

It will be understood by those skilled in the art that other plant growth hormones can be substituted for those just noted. As examples, IAA (indole-3-acetic acid), IBA (indole-3-butyric acid), and NAA (naphthalene-2-acetic acid) are effective auxins and 2-IP ($N^6$-isopentenylaminopurine) and zeatin are frequently used as cytokinins.

As an aid in comparing the present work with other published data, the following table of conversions from weight to molar concentrations might be useful.

| | 1 μM/L | 1 mg/L |
|---|---|---|
| BAP | 0.225 mg/L | 4.44 M/L |
| KIN | 0.215 | 4.65 |
| 2,4D | 0.221 | 4.52 |
| NAA | 0.816 | 5.38 |
| ABA | 0.264 | 3.78 |

In a grandparent application to the present one, Ser. No. 321,035, now U.S. Pat. No. 4,957,866, we pointed out the importance of the control of osmotic potential of the media used in the various culturing stages. A large group of chemical materials are suitable as osmoticants. In general these are highly water soluble polyhydroxylated molecules that include either simple or complex sugars, hexitols, and cyclitols. The cyclitols are normally six carbon ring compounds that are hexahydroxylated. The most readily available cyclitol is myo-inositol but any of the other eight stereoisomeric forms, such as scyllo-inositol are believed to be quite suitable. Among the sugars, sucrose and glucose are known to be very effective but many others should prove to be equally useful. Sorbitol (D-glucitol), D-mannitol, and galactitol (dulcitol) are straight chain sugar alcohols suitable as osmoticants. Lactose is a sugar effective as an osmoticant. Other materials suitable as osmoticants may include glycol ethers (polyalkylene glycols) such as poly(ethylene glycol) and poly(propylene glycol) and their respective monomers.

LOBLOLLY PINE CULTURE

EXAMPLE 1

The following schedule of treatments has been very successfully used for the growth of plantlets by somatic embryogenesis of loblolly pine (Pinus taeda). Explants were immature embryos dissected from seeds 4 to 5 weeks after fertilization. Seeds were obtained from cones supplied by a Weyerhaeuser Company seed orchard located at Washington, N.C. The cones were stored at 4° C. until used. Immediately before removal of the immature embryos the seeds were sterilized using a modified method of Gupta and Durzan (1985). Briefly, this involves an initial washing and detergent treatment followed by a first sterilization in 30% $H_2O_2$ and a second in diluted 10% v/v household bleach. The additional $HgCl_2$ treatment used by Gupta and Durzan was not found to be necessary to ensure sterility. The explants were thoroughly washed with sterile distilled water after each treatment.

Stage I—Induction

Sterile dissected embryos were placed on a solid $BM_1$ culture medium and held in an environment at 22°-25° C. with a 24 hour dark photoperiod for a time of 3-5 weeks. The length of time depended on the particular genotype being cultured. At the end of this time a white mucilaginous mass had formed in association with the original explants. This appears to be identical with that described by Gupta and Durzan (1987). Microscopic examination revealed numerous early stage proembryos associated with the mass. These are generally characterized as having a long thin-walled suspensor associated with a small head generally having less than 10 individual cells, each with dense cytoplasm and large nuclei. Early stage proembryos are illustrated in FIG. 1.

Osmolality of the induction medium may in some instances be as high as 200 mM/kg. Normally it will be below 175 mM/kg and, more typically, about 160 mM/kg or even lower. The osmolality of the medium described above was 158 mM/kg.

Stage II—Maintenance and Multiplication

Early stage proembryos removed from the masses generated in the induction stage were placed on a solid $BM_2$ medium. This differs from the induction medium in that the growth hormones (both auxins and cytokinins) were reduced by a full order of magnitude. The temperature and photoperiod were again 22°-25° C. with 24 hours in the dark. Osmolality of this medium will typically be similar or identical to that of the induction medium. In the present example it was identical. Proembryos developed in this stage were similar in appearance to those from Stage 1 and were subcultured every 12-15 days on $BM_2$ medium.

Stage III—Late Stage Proembryo Development

Early stage proembryos from either Stage I or Stage II, preferably the latter, were placed on a $BM_3$ solid medium. This medium has the same growth hormone concentrations as $BM_2$, however, the osmoticant was raised to a much higher concentration. In this case the osmoticant, myo-inositol, was at a concentration of 10,000 mg/L or 1% on a w/v basis. Osmotic potential was measured as 240 mM/kg. Temperature and photoperiod were the same as for Stages I and II. After 3 or 4 subcultures of about 12–15 days each, very robust late stage proembryos had formed. These are characterized by smooth embryonal heads generally having in the neighborhood of over 100 individual cells with multiple suspensors, as exemplified in FIG. 2. Osmotic potential of the late proembryo development medium should usually fall within the range of about 200–400 mM/kg for *Pinus taeda*. Most typically it should be in the neighborhood of about 1.5 times higher than that of the induction or multiplication media. As was noted earlier, the requirements for elevation of osmotic potential at this stage will vary for different species.

Alternatively, the Stage II and/or Stage III proembryos could be cultured for late proembryo development in suspension in a liquid medium of similar composition to $BM_3$ but lacking the agar. In this case subcultures could be made every 7–8 days.

It is preferred that early stage proembryos brought into Stage III culture should have a Stage II subculturing for rapid multiplication of the particular clone. However, on occasions where time may be of greater importance than quantity, early stage proembryos from Stage I may be taken directly into Stage III.

Stage IV—Embryo Development

The late stage proembryos from Stage III culture are transferred to either a solid or liquid $BM_4$ medium. This medium either lacks growth hormones entirely or has them present only at very low levels. However, abscisic acid (ABA) is now a necessary material for further development. The concentration of ABA should decrease over time. This decrease may be effected by inclusion of an adsorbent in the development medium, such as activated charcoal. Alternatively, in keeping with the discoveries of the present invention, the decrease may be achieved by a series of transfers to media of successively lower abscisic acid content. The term "successively lower" should be interpreted sufficiently broadly so that one or more stages in the cotyledonary development sequence might have the same level of ABA as a preceding stage as long as the start-to finish sequence has an overall decrease of the nature described.

If solid development media are used it is convenient to support the developing embryos on filter paper or a similar material for ease of transfer. If liquid media are employed a similar filter paper support may be employed and/or the embryos may be supported on absorbent polyester pads that hold the medium.

The osmotic potential of the development medium will generally be no greater than about 175 mM/kg although for some genotypes it may be advantageous to elevate it above this level. In the present case it was measured as 168 mM/kg. As before, development was carried out in complete darkness at a temperature of 22°–25° C. Development time was 4–6 weeks after which elongated cotyledonary embryos 4–5 mm long were present. These appeared as represented in FIG. 3.

Stage V—Germination

Cotyledonary embryos from Stage IV were placed on solid $BM_5$ medium for germination. This is a basal medium lacking growth hormones which has been modified by reducing sucrose, myo-inositol and organic nitrogen. After about 6–8 weeks under environmental conditions of 23°–25° C. and a 16 hour light/8 hour dark photoperiod the resulting plantlets were approximately 20 mm in length and had a well developed radicle and hypocotyl and green cotyledonary structure and epicotyl. The young plantlets are shown in FIG. 4.

Because of the reduced carbohydrate concentration, the osmotic potential of the germination medium is further reduced below that of the development medium. It will normally be below about 150 mM/kg and was, in the present example, about 100 mM/kg.

Stage VI—Plant growth

Plantlets from Stage V were removed from the culture medium and planted in a soil comprising equal parts of peat and fine perlite.

To the present time, three distinct genotypes of *Pinus taeda* have been successfully cultured through Stage V. Some of the plantlets have already been successfully transferred to soil and these are growing with good vigor. Two additional genotypes are being multiplied in Stage II prior to Stage III treatment. In work that preceded that just described, all five genotypes when cultured without the Stage III high osmoticant treatment ultimately browned and died in Stage IV. Stated differently, the method failed completely when early stage *Pinus taeda* proembryos from Stage II were taken directly into Stage IV, as is taught in the prior art.

While inorganic salts and pure simple organic chemicals generally behave similarly in culture media regardless of supplier, there are occasions when this is not the case for the more complex materials. Without intending endorsement of any product over available alternatives, chemicals from the following suppliers were used throughout the experiments to be described in the examples. Agar was obtained from Difco Laboratories, Detroit, Mich. Where specified as "tissue culture agar" the supplier was Hazleton Biologics, Inc., Lenexa, Kans. Casamino acids, a casein hydrolysate, was also supplied by Difco Laboratories. Activated charcoal was obtained from Sigma Chemical Company, St. Louis, Mo., as their grade NuC-4386.

EXAMPLE 2

The combination of ABA and activated charcoal in the Embryo Development Medium has proved to be very effective not only with *Pinus taeda* but with other important conifer species such as *Picea abies* and *Pseudotsuga menziesii*. In the following experiments the Loblolly Pine Basal Media of Tables 1 and 2 were used. In the Embryo Development Medium the ABA was adjusted as described in Table 3 and activated charcoal was included in a concentration of 2.0 g/L. All of the ingredients except the abscisic acid were combined, autoclaved, and cooled to 50°–60° C. A filter sterilized solution of ABA was then added and mixed. After 10 minutes the medium was poured into petri dishes.

Late stage proembryo cells of two loblolly pine genotypes, grown as described in the first example, were settled from a suspension culture, the supernatant liquid poured off, and 1-1.5 mL of the settled cells were plated on the solid Embryo Development Medium in 5 cm dishes. These cultures were incubated in the dark at about 22° C. for six weeks. Control cultures having 2 and 4 mg/L ABA without activated charcoal were also prepared. The following results were obtained.

TABLE 3

| Medium Composition | | Embryos Produced | |
|---|---|---|---|
| ABA, mg/L | Activated Charcoal, g/L | Genotype A | Genotype B |
| 2.0 | 0.0 | 2.5 | — |
| 4.0 | 0.0 | 5.5 | — |
| 20.0 | 2.0 | 0 | 0 |
| 40.0 | 2.0 | 2 | 2 |
| 60.0 | 2.0 | 4 | 3 |
| 80.0 | 2.0 | 10 | 4.5 |
| 100.0 | 2.0 | 8.5 | 2 |

The embryos produced on the charcoal containing media were of better morphology with a well developed cotyledonary structure but without evidence of germinating precociously when compared to those grown without activated charcoal in the medium. The media described here are not represented as being optimized for the species or any genotype.

As an alternative procedure, the late stage proembryos are also placed on polyester pads containing 9-10 mL of a liquid charcoal-free development medium containing initially 8.0 mg/L ABA and cultured for about 7-10 days. They are then transferred sequentially for similar time intervals to media containing 4.0, 2.0 and 1.0 mg/L ABA. Embryos of good quality are produced although, in some cases, in smaller numbers than was noted when activated charcoal was included in the medium.

NORWAY SPRUCE CULTURE

EXAMPLE 3

Some coniferous species are relatively easier to propagate by somatic embryogenesis than others. Coastal redwood, Sequoia sempervirens, is considered to be a relatively easy species while Norway spruce, Picea abies, is usually thought to be of only moderate difficulty. Most members of the genus Pinus as well as Douglas-fir, Pseudotsuga menziesii, are regarded as very difficult. This has posed a major challenge to researchers since the latter two genera include a major percentage of the worlds most economically important timber species. Even though past researchers have reported success with somatic embryogenesis of several pines and of Douglas-fir, others in the field have frequently not been able to duplicate the work of these competent investigators. There are probably several reasons for this. Most certainly, one of them is over optimism on the part of researchers who have achieved and reported early stage embryogenesis or embryo-like structures but who later have not been able to succeed in producing significant numbers of cotyledonary embryos or plantlets. Another is the great differences in performance between different genotypes within a given species. Picea abies is a case in point. As noted earlier it is usually regarded as a species of only moderate difficulty to reproduce by somatic embryogenesis using present state-of-the-art technology. However, there are some genotypes of Picea abies that haven proven intractable to all previous efforts. Most researchers have limited themselves to working with only one or two genotypes that are known from past experience to give good results.

Figure 5:
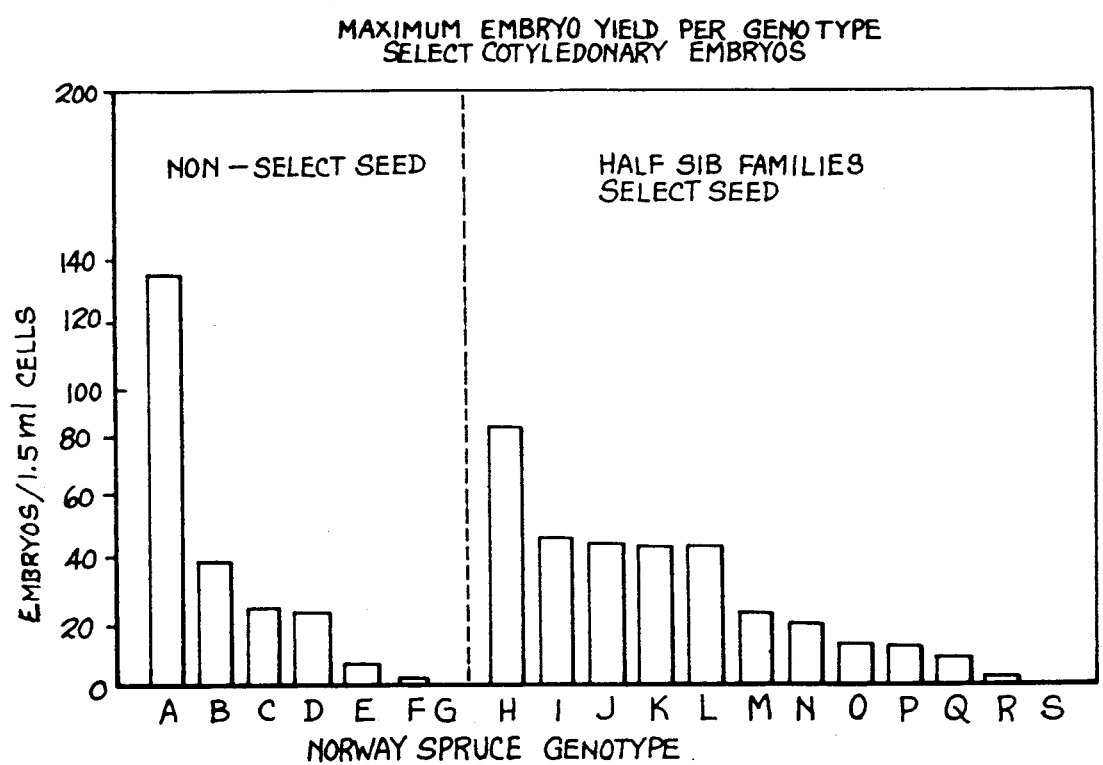
FIG. 5 shows the variation in behavior in tissue culture of various genotypes of a single coniferous species.

Our method has resulted in successful production of late stage proembryos and cotyledonary embryos on 23 of the 26 genotypes of Picea abies that have been initiated in culture to date. This sample includes a considerable number of previously intractable genotypes. FIG. 5 shows the maximum yield of embryos per culture plate for 19 genotypes grown on the same nonoptimized culture (Medium No. 2 as described in Example 6). Seven of these are from non-select wild seed and twelve are select seed from known half-sib orchard families. The enormous differences in behavior constituting two full orders of magnitude, especially within the non-select seed, are immediately apparent. As has been noted earlier, similar results have been obtained with Pinus taeda, although not all genotypes have been processed to the later stages of treatment at the present time.

While the plant growth hormone usages noted in Table 2 are near optimum for loblolly pine, different concentrations and mixtures may prove more suitable for other species. It is fairly well established that growth hormones are usually necessary in Stages I-III, although some workers have apparently achieved early stage proembryos using growth hormone-free media. However, even when initially cultured on hormone-free media, these early stage proembryos were then transferred to cultures having the usual growth hormones. These hormones may in some instances be a single auxin or a mixture of auxins with or without one or more cytokinins. As a general rule the total concentration of all growth hormones should be below about 250 $\mu$M/L, preferably below about 100 $\mu$M/L in the Stage I medium. These concentrations should be reduced about tenfold in the Stage II and Stage III media.

The following tables show preferred media for culture of Norway spruce by somatic embryogenesis.

TABLE 4

| | Picea Abies Basic Culture Media | |
|---|---|---|
| | Concentration, mg/L | |
| Constituent | A[1] | B[2] |
| BASAL SALTS | | |
| NH$_4$NO$_3$ | — | 206.3 |
| KCl | 372.5 | — |
| KNO$_3$ | 50.0 | 2340.0 |
| KH$_2$PO$_4$ | 85.0 | 85.0 |
| MgSO$_4$.7H$_2$O | 160.0 | 185.0 |
| CaCl$_2$.6H$_2$O | 220.0 | 220.0 |
| KI | 0.415 | 0.415 |
| H$_3$BO$_3$ | 3.10 | 3.10 |
| MnSO$_4$.H$_2$O | 8.45 | 8.45 |
| ZnSO$_4$.7H$_2$O | 4.30 | 4.30 |
| NaMoO$_4$.2H$_2$O | 0.125 | 0.125 |
| CuSO$_4$.5H$_2$O | 0.0125 | 0.0125 |
| CoCl$_2$.6H$_2$O | 0.0125 | 0.0125 |
| FeSO$_4$.7H$_2$O | 13.90 | 13.93 |
| Na$_2$EDTA | 18.65 | 18.63 |
| ORGANIC ADDITIVES | | |
| Sucrose | 10,000. | 30,000. |
| myo-Inositol | 50.0 | 1000.0 |
| Casamino acids | — | 500.0 |
| L-Glutamine | 750.0 | 450.0 |
| Thiamine.HCl | 0.05 | 1.00 |
| Pyridoxine.HCl | 0.05 | 0.50 |
| Nicotinic acid | 0.25 | 0.50 |
| Glycine | — | 2.00 |
| L-Asparagine | 50.0 | — |
| pH | 5.8 | 5.7 |

[1] Institute of Paper Chemistry medium (Verhagen and Wann 1989)
[2] Gupta and Durzan medium BM$_3$ (1986b).

TABLE 5

Composition of *Picea Abies* Media for Different Stage Treatments

BM$_I$ Induction Medium
  BM$_A$[1] + NAA[3] (10.8 μM) + BAP[4] (4.4 μM) + 7.0 g/L Difco agar.
BM$_M$ Maintenance and Multiplication Medium
  Bm$_B$[2] + 2,4-D[5] (5 μM) + BAP (2 μM) + KIN[6] (2 μM). 6.0 g/L Difco agar added if solid medium is desired.
BM$_D$ Cotyledonary Embryo Development Medium
  BM$_B$ + 40.0 mg/L Arginine + 100 mg/L Asparagine + 6.0 g/L Tissue Culture Agar + Abscisic acid (as specified) + Adsorbent (e.g., activated charcoal) (as specified). KNO$_3$ is reduced to 1170 mg/L in basal salts.
BM$_G$ Germination Medium
  BM$_B$ with KNO$_3$ reduced to 1170 mg/L, myo-Inositol reduced to 100 mg/L, Sucrose reduced to 20.0 g/L, and L-Glutamine and Casamino acids removed. 2.5 g/L of Adsorbent and 6.0 g/L of Tissue Culture Agar are added.

[1] Basal medium A from Table 4
[2] Basic medium B from Table 4
[3] 2-Naphthylacetic acid (Naphthalene-2-acetic acid)
[4] N$^6$-Benzylaminopurine
[5] 2,4-Dichlorophenoxyacetic acid
[6] Kinetin Our earlier applications U.S. Pat. Nos. 5,034,326 and 5,036,007.2, now U.S. Patents and, showed that Norway spruce cotyledonary embryos could be developed on a medium containing abscisic acid alone or ABA in combination with activated charcoal. However, the use of activated charcoal was very desirable for optimum embryo production and quality. In most cases, no embryos were produced when charcoal was omitted.

In view of present understanding of the mode of action of activated charcoal a number of previous experiments were repeated starting with Norway spruce late stage proembryos. As has been noted before, the action of the charcoal causes a gradual reduction in ABA level throughout the cotyledonary embryo development period. This reduction follows a generally exponential curve. Adsorption of ABA is very rapid initially but slows significantly over time. It now appears probable that relatively low levels of ABA should be present at the end of the development period. In some cases this may be an absolute requirement if good quality embryos are to be produced in useful quantities. Failure to recognize this may have been one reason for the poor success when charcoal was absent in the development medium. By maintaining a relatively high level of ABA throughout the development period an adverse toxic environment may have been created. If this hypotheses is correct, other means of reducing ABA level during the development period should give results equivalent to the use of media containing an ABA adsorbent.

EXAMPLE 4

In order to test the above hypothesis late stage Norway spruce Genotype 682 proembryos were cultured using development media with and without charcoal. Cultures made without charcoal were transferred every two weeks to fresh development media having an adjusted ABA content. In some cases this level was maintained constant and in others it was sequentially reduced.

Mature *Picea abies* seed embryo explants were cultured on an Initiation Medium and Maintenance Medium as described in Tables 4 and 5. Explants were incubated in light of an intensity approximately 50 μEm$^{-2}$sec$^{-1}$. In this case the Induction Medium BM$_I$ had a relatively low carbohydrate content with a resulting low osmolality of about 90 mM/kg. After an early stage embryogenic mass had developed, it was transferred to a solid and later to a liquid Maintenance and Multiplication Medium BM$_M$ having a higher osmolality of about 158 mM/kg. In this case the proembryos had attained a sufficiently late stage of development without the need for further culturing on a very high osmotic potential Late Proembryo Development Medium. These proembryos were drained onto a porous pad and equal portions plated onto one of three solid development medium formulations. After two weeks the growing embryos were transferred to fresh medium. Then after two more weeks another transfer was made. Cultures were evaluated after six weeks culturing time. No transfers were made in the control experiment using 0.125% activated charcoal in the medium. Media compositions and results are given in the following table.

TABLE 6

| Experiment Number | ABA Sequence[1] | Charcoal, % | Mean No. Embryos | Standard Error |
|---|---|---|---|---|
| 1 | 50[2] | 0.1 | 73.5 | 8.3 |
| 2 | 10/10/10 | 0 | 35.0 | 5.7 |
| 3 | 10/10/5 | 0 | 44.3 | 5.1 |
| 4 | 10/5/2.5 | 0 | 48.5 | 4.8 |
| 5 | 5/5/5 | 0 | 29.5 | 3.3 |
| 6 | 5/5/2.5 | 0 | 30.8 | 5.5 |
| 7 | 5/2.5/1 | 0 | 34.8 | 5.3 |

[1] ABA is expressed in mg/L.
[2] No medium transfers made in Experiment No. 1.

While less embryos were produced without charcoal, embryo quality was equivalent. In all cases, stepwise reduction of ABA resulted in greater numbers of embryos compared with cultures in which ABA was not reduced. No representation is made that conditions were optimum for this genotype. It is possible that an even higher starting level of ABA followed by stepwise reduction would produce numbers equivalent to the charcoal culture.

To the present time, using all of the procedures outlined, about 3800 plantlets of *Picea abies* have been produced from 20 different genotypes of the species and established in soil.

DOUGLAS FIR CULTURE

Figure 6:
FIG. 6 is a photomicrograph of a clump of Douglas-fir early proembryos.

As noted in the background discussion, the embryogeny of Douglas-fir is quite different from trees such as the spruces or pines. One of these differences is seen when early stage proembryos are placed in or on a late stage proembryo development medium. Instead of single late stage embryos, Douglas-fir develops tight clumps of these embryos, as is shown in the photomicrograph of FIG. 6. Upon further development into cotyledonary embryos, these clumps remain united and the resulting product is difficult to work with for further conversion (FIG. 7). This phenomenon had apparently been recognized earlier by Durzan and Gupta (1987) who, while they did not discuss it specifically, transferred their embryonal-suspensor masses to a liquid shake culture containing 0.5 μM abscisic acid. They note that under the influence of ABA, individual bipolar embryos were produced which were then transferred to a development medium without ABA. The present method utilizes a liquid shake culture with reduced osmotic level and added abscisic acid between late proembryo development and cotyledonary embryo development to achieve the necessary singulation. Osmotic level is again raised to levels generally above about 450 mM/kg during the final cotyledonary embryo development stage or stages.

A reformulated basal culture medium has been developed by the present inventors specifically to give more successful initiation and multiplication of Douglas-fir. Preferred media compositions are given in the following tables. A number of ingredients are varied in quantity, such as those that affect the level and balance between organic and inorganic nitrogen, depending on the response of individual genotypes. This response cannot be readily predicted and media optimization must largely be achieved by a combination of intuition and trial and error.

TABLE 7

*Pseudotsuga Menziesii* Basic Culture Media

| Constituent | Concentration, mg/L | |
|---|---|---|
| | WTC[1] | BM$_G$[2] |
| BASAL SALTS | | |
| NH$_4$NO$_3$ | — | 206.3 |
| KNO$_3$ | varies[1] | 1170.0 |
| CaCl$_2$.6H$_2$O | 200.0 | 220.0 |
| Ca(NO$_3$)$_2$.2H$_2$O | varies[1] | — |
| KH$_2$PO$_4$ | 340.0 | 85.0 |
| MgSO$_4$.7H$_2$O | 400.0 | 185.0 |
| MnSO$_4$.H$_2$O | 20.8 | 8.45 |
| ZnSO$_4$.7H$_2$O | 8.0 | 4.30 |
| CuSO$_4$.5H$_2$O | 0.024 | 0.013 |
| FeSO$_4$.7H$_2$O | 27.85 | 13.93 |
| Na$_2$EDTA | 37.25 | 18.63 |
| H$_3$BO$_3$ | 5.0 | 3.10 |
| NaMoO$_4$.2H$_2$O | 0.20 | 0.125 |
| CoCl$_2$.6H$_2$O | 0.025 | 0.0125 |
| KI | 1.00 | 0.42 |
| ORGANIC ADDITIVES | | |
| myo-Inositol | varies[1] | 100.0 |
| Thiamine.HCl | 1.00 | 1.00 |
| Nicotinic acid | 0.50 | 0.50 |
| Pyridoxine.HCl | 0.50 | 0.50 |
| Glycine | 2.00 | 2.00 |
| L-Glutamine | varies | 450.0 |
| Casamino acids | 500.0 | — |
| Sucrose | varies | 20,000. |
| pH | 5.7 | 5.7 |

[1] Usage varies according to culturing stage and genotype.
[2] Modified Gupta and Durzan medium BM$_3$ (1986b). Medium BM$_G$ of application Serial No. 426,331.

velopment. This level will differ somewhat between genotypes within each species as it does between species. Similarly, the level of abscisic acid present should be gradually reduced during the cotyledonary embryo development period. This may be done either by the inclusion of activated charcoal in the medium or by a stepwise reduction effected by multiple transfers to media of successively lower ABA concentration. In the case of Douglas-fir that requires a singulation stage between late proembryo development and cotyledonary embryo development, the ABA level is preferably continuously reduced from that present at the beginning of the singulation stage.

The examples that follow represent the best mode known at present for culturing Douglas-fir by somatic embryogenesis. These examples are all directed to the singulation and cotyledonary embryo development stages. The steps prior to that time are similar to those used for loblolly pine and Norway spruce with the exceptions of the somewhat reformulated media. These earlier steps will be briefly outlined.

EXAMPLE 5

A preferred explant for Douglas-fir is an immature zygotic embryo. Best results have been realized with embryos selected in the interval just prior to the development of an apical dome up to the time just before cotyledon primordia become visible. The cones are split longitudinally and seeds isolated from young ovuliferous scales. Seeds are sterilized by first being agitated in 10% Liqui-Nox laboratory cleaner (Alconox, Inc, New York, N.Y.) with a small additional amount of liquid surfactant for about 10 minutes. They are then rinsed in running tap water for 30 minutes. At this time they are transferred to a sterile hood and agitated in 20% H$_2$O$_2$ for 10 minutes. Following five rinses in sterile deionized water the seed coat is split and the female gametophyte removed. This is split on one side and the embryo teased out while still remaining attached to the gametophyte by the suspensor. An explant so prepared is placed on the Stage I solid initiation medium in a 50 mm petri dish. The explants are incubated in the dark from 4–8 weeks. Success in forming an embryonal-suspensor mass

TABLE 8

| | Stage I Initiation | Stage II Maintenance 1 | Stage III Maintenance 2 | Stage IV Singulation | Stage V Development | Stage VI Germination |
|---|---|---|---|---|---|---|
| Basal Medium | WTC | WTC | WTC | WTC | WTC | BM$_G$ |
| KNO$_3$ | 1250[1] | 1250–2500 | 1250 | 1050 | 2000–2500 | 1170 |
| Ca(NO$_3$)$_2$.2H$_2$O | — | — | — | 200 | — | — |
| myo-Inositol | 1000 | 1000 | 100–30,000 | 100 | 100 | 100 |
| L-Glutamine | 450 | 450 | 1000 | 1000 | 750–1500 | — |
| Amino acid mixture[2] | — | — | — | — | 290 | — |
| Sucrose | 15,000 | 30,000 | 30,000 | 20,000 | 20,000–60,000 | 20,000 |
| Supp. carbohydrate | — | — | — | — | 30,000–300,000 | — |
| 2,4-D | 110 | 1.1 | 1.1 | — | — | — |
| N$^6$-Benzyladenine | 45 | 0.22 | 0.22 | — | — | — |
| Kinetin | 43 | 0.22 | 0.22 | — | — | — |
| Abscisic acid | — | — | — | 0–15 | 0–50 | — |
| Activated charcoal | 2500 | — | — | — | 0–2500 | 2500 |
| Agar | 5000 | 5000 | — | — | — | 8000[4] |
| Gelrite | — | — | — | — | 3000[3] | — |

[1] All units are in mg/L (or ppm).
[2] L-Proline - 100, L-Asparagine - 100, L-Arginine - 50, L-Alanine - 20, L-Serine - 20.
[3] Not used for liquid media.
[4] Tissue culture agar.
The pH of all media are adjusted to 5.7.

It will be seen by reference to the media compositions that the features of the earlier inventions described in our parent applications are advantageously used with Douglas-fir. As with loblolly pine, a raised osmotic pulse is desirable for good quality late proembryo de- (ESM) containing proembryos varies from about 1–7% depending on a number of variable factors which presently are not well understood.

All stages of culture are carried out at temperatures which may vary between about 20°-25° C. Temperature is not generally critical and may, on occasion be varied so as to fall outside this range.

The embryonal-suspensor masses containing early stage proembryos are transferred to a solid Stage II maintenance and multiplication medium containing greatly reduced plant growth hormones and preferably a somewhat raised osmotic level. Again, culturing is carried out in the dark with subcultures made at no greater than about two week intervals. The clone can be maintained at this stage for long periods of time.

Early stage proembryos from the multiplication step are transferred to a liquid Stage III second maintenance medium Having a significantly raised osmotic level. This corresponds to the raised osmotic pulse found so beneficial for loblolly pine. It is similarly advantageous for Douglas-fir. However, a slightly lower osmotic level of at least about 170 mM/kg will usually suffice for Douglas-fir although some genotypes may require levels as high as 240 mM/kg. Myo-inositol, which will normally be around 5000 mg/L, may need to be adjusted somewhat depending on the needs of the particular genotype in order to obtain optimum results. Culture is carried out in the dark and is periodically subcultured, usually weekly. Robust late stage proembryos having 100 or more cells will develop during this time.

Following late proembryo development, the cultures are transferred to a Stage IV liquid medium for the singulation step referred to earlier. This has a reduced osmotic level and is free of auxins and cytokinins. Abscisic acid is a newly added hormone in an initial amount in the range of about 5-15 mg/L, more usually about 5-10 mg/L. Cultures are again carried out in the dark. From two to four subcultures are made on a weekly basis. The level of exogenous abscisic acid will drop somewhat during each subculture. It is generally preferred that the level of abscisic acid at the beginning of a new subculture not be significantly higher than the level at the end of the previous subculture. Preferably it will be lower. This will result in an essentially continuous drop in ABA level over the singulation period and this continuous decrease in level will continue through the development period. At this time the embryos are ready to complete development to cotyledonary embryos. They are transferred to either a solid medium or supported on a liquid medium with an effective abscisic acid level which is preferably lower than that at the end of the final singulation subculture. Most typically this will not exceed about 5 mg/L effective ABA and it will usually not exceed 2.5 mg/L and may be even lower. In some cases it is not necessary to add any exogenous ABA to the development medium since a sufficient amount will be carried over with the residual singulation or rinse medium accompanying the embryos when the transfer is made from the last singulation stage. It has been found preferable for Douglas-fir to carry out development cultures entirely in the dark. A typical series of media beginning at the singulation stage and through cotyledonary embryo development might have 10, 5, 2.5, and 1 mg/L ABA or 10, 5, 2.5, 1 and 0 mg/L ABA. Activated charcoal may be used in the development medium to effect the necessary ABA reduction but it is not essential. Particularly for Douglas-fir, a raised osmotic level in the development medium is very highly desirable. Osmotic levels should be above about 400 mM/kg and for some genotypes may advantageously be considerably higher. The effect of osmotic level is discussed in detail in our earlier application U.S. Pat. No. 5,036,607, which is herein incorporated by reference.

EXAMPLE 6

Late stage Douglas-fir proembryos of several genotypes were grown as described above. These were subcultured into a gently agitated liquid Stage IV singulation medium containing 10 mg/L abscisic acid. After about one week the embryos were again subcultured into a fresh singulation medium containing 5 mg/ ABA. In similar fashion, a third transfer was made to a singulation medium having 2.5 mg/L ABA. At the end of the third week some cultures were transferred to polyester pads saturated with liquid Stage V development medium. Others were transferred to a fourth singulation medium having 1 mg/L ABA prior to transfer to development medium.

The embryos transferred to development medium after three weeks of singulation were first rinsed in development medium lacking any supplemental carbohydrate but containing 1.25 mg/L ABA. The cells were settled and the supernatant medium drained and discarded. They were again rinsed using a volume of the same medium equal to the cell volume. The cells were settled again and half of the supernatant medium removed. Cells were then resuspended to give a mixture of 2 parts settled cells and 1 part fresh rinse medium. Then 1.5 mL of cell suspension was plated on double polyester pads saturated with 9-10 mL of development medium lacking exogenous abscisic acid and having activated charcoal varying between 0% and 0.1% and polyethylene glycol 8000 varying between 20% and 26% as the inert supplemental carbohydrate for osmotic regulation.

Those embryos transferred to development medium after four weeks of singulation were treated similarly with the exception that the rinse medium did not contain any ABA.

Development proceeded for about 4-6 weeks in the dark without medium change. Results are shown in Table 9 as follows:

TABLE 9

Effect of Activated Charcoal in Development Medium

| Genotype | Singulation Time, weeks | PEG, % | Activated Charcoal, % | Embryos Formed |
|---|---|---|---|---|
| 711 | 3 | 25 & 26[(1)] | 0 | 60-80 |
| 711 | 4 | 23 | 0.1 | 30-40 |
| 711 | 4 | 24 | 0.1 | 30-40 |
| 711 | 4 | 25 | 0.05 | 30-40 |
| 711 | 4 | 25 | 0.1 | 30-50 |
| 711 | 4 | 25 & 26 | 0 | 40-50 |
| 711 | 4 | 26 | 0.1 | 30-40 |
| 732 | 3 | 24 & 25[(2)] | 0 | 50-80 |
| 732 | 4 | 22 | 0 | 15-25 |
| 732 | 4 | 24 & 25 | 0 | 30-50 |
| 735 | 3 | 25 & 26 | 0 | 60-80 |
| 735 | 4 | 25 & 26 | 0 | 30-40 |

[(1) & (2)]No significant differences were found in any of the cultures having 24% or 25% PEG or 25% or 26% PEG when all other conditions were similar.

Visual evaluation of embryo quality indicated that there was little difference between embryos that had three or four weeks in the singulation stage. All had good quality. The embryos from cultures without activated charcoal in the development medium appeared to be of better quality than those formed when charcoal was present.

EXAMPLE 7

An experiment similar to the above was repeated using three different singulation treatments, embryo development media with and without activated charcoal, and including two additional Douglas-fir genotypes. The first singulation treatment used sequential liquid media containing 10 and 5 mg/L ABA, the medium being changed at a one week interval. The next singulation treatment added a third stage of 5 mg/L ABA. The third singulation treatment was similar to the second except that the third stage also contained 0.1 mg/L of the auxin IBA (indole-3-butyric acid). Singulated embryos were placed on one of two development media. Both were formulated according to the Stage 5 medium of Table 8 and contained 17.5% polyethylene glycol 8000 and 5% lactose with ABA being omitted. One (medium 5163) contained 0.1% w/v activated charcoal while the other (medium 5516) lacked charcoal.

The final development culture was carried out on polyester pads as noted in Example 6. In the present case only one rinse was used. The cells were settled and drained and an equal volume of development medium containing 2.5 mg/L ABA was added. The rinse medium lacked any additional osmoticants (polyethylene glycol or lactose). Cells were again settled and half of the supernatant medium drained off. The resulting mixture was mixed and 1 mL pipetted onto the pad. After about 4 weeks culturing the embryos were counted and graded. Four replicates were made at each culturing condition. Results are given in the following table.

TABLE 10

| ABA Pretreatment | Culture Medium | Activated Charcoal, % | Genotype 735 | Genotype 711 | Genotype 771 |
|---|---|---|---|---|---|
| 10/5 | 5163 | 0.1 | 57.8 ± 17.8 | — | 13.0 ± 5.0 |
| 10/5 | 5516 | 0 | 10.0 ± 2.0 | — | 0 |
| 10/5/5 | 5163 | 0.1 | 51.5 ± 10.0 | 17.5 ± 3.1 | — |
| 10/5/5 | 5516 | 0 | 11.0 ± 2.0 | 5.8 ± 0.9 | — |
| 10/5/5/IBA | 5163 | 0.1 | 49.3 ± 5.3 | 31.0 ± 18.6 | 10.3 ± 3.5 |
| 10/5/5/IBA | 5516 | 0 | 3.3 ± 0.6 | 3.3 ± 0.3 | 11.3 ± 5.4 |

Again, embryo quality using development medium without charcoal was equivalent to that when activated charcoal was included. With the exception of genotype 771, significantly lower quantities of embryos were produced. There is no representation made here that the culturing conditions were optimized for any of the genotypes tested.

Thus, as was noted before, the use of activated charcoal in cotyledonary embryo development media for ABA level control is usually advantageous. However, there appear to be conditions where control of ABA level by stepwise reduction in development media lacking charcoal might be preferred.

It would appear that an osmotic level above about 450 mM/kg may be a threshold value for Douglas-fir embryo development media if the best yield and quality are to be obtained. This level is one measured at the end of the development period rather than the beginning. Ideally, it is believed advantageous for the osmotic level to rise somewhat over the period of development. It is possible to control osmotic level during development by periodic medium changes. To facilitate this without disturbance to the developing embryos they may be supported on a material such as filter paper which is placed directly on either a solid culture medium or on the saturated pad of a liquid medium.

It also appears important for Douglas-fir to have a level of available exogenous abscisic acid that drops essentially continuously from the initial usage at the beginning of the singulation stage to the end of the development period. An initial level at the beginning of singulation of about 5-15 mg/L appears suitable. This will decrease to a low level at the end of the development stage. Exact measurements have not been possible at the end of development due to the limitations of available analytical techniques.

Following embryo development the somatic embryos may be retained for some period of time in cold storage. They may be converted into artificial seeds for field or nursery planting. Alternatively, they may be placed immediately on a germination medium such as Medium $BM_G$ (Tables 7 and 8) for conversion into plantlets prior to planting in soil.

Figure 10:
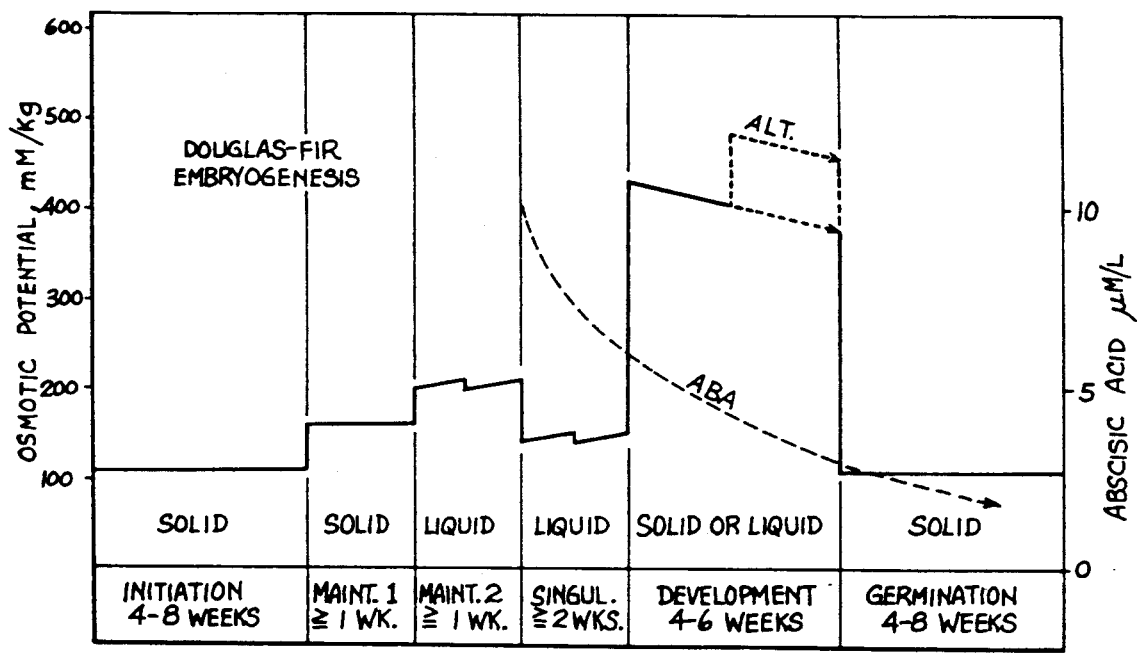
FIG. 10 is a graph showing typical levels of osmotic potential and abscisic acid concentration during the culture of Douglas-fir.

FIG. 10 contains somewhat idealized curves for Douglas-fir showing the osmotic levels and abscisic acid level at each of the various stages from initiation through germination. It has been observed that the osmotic level will increase somewhat during each liquid shake stage of late proembryo development and singulation. The opposite phenomenon seems to occur during development, probably due to utilization of sucrose and other nutrients. Taking this drop into account is necessary in adjusting the initial osmotic level of the development media. Here the solid portion of the curve represents the normal course of osmotic level if no media changes are made. The dotted portion shows how osmotic level can be increased if one or more transfers to fresh media are made.

To date about 2000 genotypes have been initiated in culture and are being held in the maintenance stage. From earlier work, over 2000 converted seedlings have been produced from 13 genotypes of Douglas-fir and are growing in soil.

It should be recognized that there is not one single set of culturing conditions that will be suitable for achieving somatic embryogenesis of all species or for all genotypes within a species. Tissue culture as a whole is a highly unpredictable science. This statement has even greater applicability to somatic embryogenesis. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the art of tissue culture. The important discovery of the present invention is the need for a decreasing level of abscisic acid during the period of cotyledonary embryo development. This can be achieved by the inclusion of an adsorbent such as activated charcoal in the medium during the growth of late stage proembryos to cotyledonary embryos. Alternatively, transfers can be made to media of successively lower ABA content during the time of cotyledonary embryo development. These procedures have given results that are far superior in terms of success and consistency than any process reported heretofore. The process has been successfully applied to all of the several species and many genotypes of coniferous plants studied to date and appears to be of general use for all coniferous species.

It will be understood that many variations can be made in the procedures described for the various culturing stages while still remaining within the spirit of the present invention. It is the intention of the inventors that such variations should be included within the scope of their invention if found defined within the following claims.

BIBLIOGRAPHY

Abo El-Nil, Mostafa, 1980. Embryogenesis of gymnosperm forest trees. U.S. Pat. No. 4,217,730.

Becwar, M. R. and R. P. Feirer, 1989. Factors regulating loblolly pine (*Pinus taeda* L.) somatic embryo development. *Institute of Paper Chemistry Report*, Southern Forest Tree Improvement Conference, Raleigh, N.C., June 1989.

Becwar, M. R., Nagmani, and S. R. Wann, 1990. Initiation of embryogenic cultures and somatic embryo development in loblolly pine (*Pinus taeda*). *Canadian Journal of Forest Research* 20: 810–817.

Becwar, M. R., T. L. Noland, and S. R. Wann, 1987. A method for quantification of the level of somatic embryogenesis among Norway spruce callus lines. *Plant Cell Reports* 6: 35–38–.2.

Becwar, M. R., S. R. Wann, and R. Nagmani, 1988. A survey of initiation frequency of embryogenic callus among ten families of *Pinus taeda* (loblolly pine). *Abstracts*, 4th International Conifer Tissue Culture Work Group, Aug. 8–12, 1988, Saskatoon, Saskatchewan, Canada.

Boulay, M. P., P. K. Gupta, P. Krogstrup, and D. J. Durzan, 1988. Development of somatic embryos from cell suspension cultures of Norway spruce (*Picea abies* Karst.). *Plant Cell Reports* 7: 134–137.

Bourgkard, F. and J. M. Favre, 1988. Somatic embryos from callus of *Sequoia sempervirens*. *Plant Cell Reports* 7: 445–448.

Buchheim, Julie A., Susan M. Colburn, and Jerome P. Ranch, 1989. Maturation of soybean somatic embryos and the transition to plantlet growth. *Plant Physiology* 89: 768–775.

Durzan, D. J. and P. K. Gupta, 1987. Somatic embryogenesis and polyembryogenesis in Douglas-fir cell suspension cultures. *Plant Science* 52: 229–235.

Finer, John J., Howard B. Kriebel, and Michael R. Becwar, 1989. Initiation of embryogenic callus and suspension cultures of eastern white pine (*Pinus strobus* L.). *Plant Cell Reports* 8: 203–206.

Gupta, Pramod K. and Don J. Durzan
 1985: Shoot multiplication from mature trees of Douglas-fir (*Pseudotsuga menziesii*) and sugar pine (*Pinus lambertiana*). *Plant Cell Reports* 4: 177–179.
 1986a: Somatic polyembryogenesis from callus of mature sugar pine embryos. *Bio/Technology* 4: 643–645.
 1986b: Plantlet regeneration via somatic embryogenesis from subcultured callus of mature embryos of *Picea abies* (Norway spruce). *In Vitro Cellular and Development Biology* 22: 685–688.
 1987: Biotechnology of somatic polyembryogenesis and plantlet regeneration in loblolly pine. *Bio/Technology* 5: 147–151.

Hakman, Inger and Sara von Arnold
 1985: Plantlet regeneration through somatic embryogenesis in *Picea abies* (Norway spruce). *Journal of Plant Physiology* 121: 149–158.
 1988: Somatic embryogenesis and plant regeneration from suspension cultures of *Picea glauca* (White spruce). *Physiologia Plantarum* 72: 579–587.

Hakman, Inger, Larry C. Fowke, Sara von Arnold, and Tage Eriksson, 1985. The development of somatic embryos in tissue cultures initiated from immature embryos of *Picea abies* (Norway spruce). *Plant Science* 38: 33–35.

Johansson, Lars, 1983. Effects of activated charcoal in anther cultures. *Physiologia Plantarum* 59: 397–403.

Johansson, Lars, Barbro Andersson, and Tage Eriksson, 1982. Improvement of anther culture technique: activated charcoal bound in agar medium in combination with liquid medium and elevated $CO_2$ concentration. *Physiologia Plantarum* 54: 24–30.

Lu, Chin-Yi, and Trevor A. Thorpe, 1987. Somatic embryogenesis and plantlet regeneration in cultured immature embryos of *Picea glauca*. *Journal of Plant Physiology* 28: 297–302.

Murashige, Toshio and Folke Skoog, 1962. A revised medium for rapid growth and bioassays with tobacco tissue cultures. *Physiologia Plantarum* 15: 473–493.

Nagmani, R. and M. R. Becwar, 1988. Factors affecting somatic embryo development in loblolly pine. *Abstracts*, 4th International Conifer Tissue Culture Work Group, Aug. 8–12, 1988, Saskatoon Saskatchewan, Canada.

Nagmani, R. and J. M. Bonga, 1985. Embryogenesis in subcultured callus of *Larix decidua*. *Canadian Journal of Forest Research* 15: 1088–1091.

Raghavan, V. N., 1986. *Experimental Embryogenesis*, p 100, McMillan, N.Y.

Schuller, Astrid and Gerhard Reuther, 1989. Response of *Abies alba* embryonal-suspensor mass to various carbohydrate treatments. *Somatic Cell Genetics Working Party S2-04-07 and NATO Advanced Research Workshop on Woody Plant Biology*, Institute of Forest Genetics lacerville California, Oct. 15–19, 1989 (Abstract).

Singh, Hardev, 1978. "Embryo" in *Embryology of Gymnosperms*, Chapter 11, Gebruder Borntrager, Berlin.

Teasdale, Robert D., Pamela A. Dawson, and Harold W. Woolhouse, 1986. Mineral nutrient requirements of a loblolly pine. (*Pinus taeda*) cell suspension culture. *Plant Physiology* 82: 942–945.

Verhagen, S. and S. R. Wann, 1989. Norway spruce somatic embryogenesis: high frequency initiation from light-cultured mature embryos. *Plant Cell Tissue and Organ Culture* 16: 103–111.

Von Arnold, Sara, 1987. Improved efficiency of somatic embryogenesis in mature embryos of *Picea abies* (L.) Karst. *Journal of Plant Physiology* 128: 233–244.

Von Arnold, Sara and Inger Hakman, 1988. Regulation of somatic embryo development in *Picea abies* by abscisic acid (ABA). *Journal of Plant Physiology* 132: 164–169.

Yeung, Edward C. and D. C. W. Brown, 1982. The osmotic environment of developing embryos of Phaseolus vulgaris. *Z. Pfanzenphysiol. Bd.* 106: 149–156.

Ziv, Meira and Geula Gadasi, 1986. Enhanced embryogenesis and plant regeneration from cucumber (*Cucumis sativus* L.) callus by activated charcoal in solid/liquid double-layer cultures. *Plant Science* 47: 115–122.

We claim:

1. A method of reproducing coniferous plants by somatic embryogenesis which comprises:

placing an explant on an induction culture medium containing nutrients and plant growth hormones sufficient to cause the explants to form somatic proembryos;

transferring the proembryos to an initial cotyledonary embryo development medium containing exogenous abscisic acid in the range of about 5–100 mg/L; and controlling the concentration of abscisic acid over time by again transferring the developing embryos at least once to a fresh development medium containing an amount of abscisic acid reduced below that present in the initial development medium, so that a reduction of exogenous abscisic acid occurs during the period of cotyledonary embryo development, the final development medium having abscisic acid in a range no greater than about 0–10 mg/L.

2. The method of claim 1 which further includes transferring the proembryos from the induction culture medium to an intermediate maintenance and multiplication culture medium prior to transferring the proembryos to the cotyledonary embryo development medium, the intermediate medium having a level of plant growth hormones reduced up to about two orders of magnitude below the concentration in the induction medium.

3. The method of claim 2 which further includes transferring the proembryos from the maintenance and multiplication medium into a late stage proembryo development medium prior to transferring the proembryos to the cotyledonary embryo development medium, the late stage medium having an osmotic potential in the range of about 170–400 mm/kg.

4. The method of claims 1, 2, or 3 in which at least two transfers occur following the initial culture in cotyledonary embryo development medium to development media having an abscisic acid level reduced below that of the initial development medium.

5. The method of claim 4 in which at least three transfers occur.

6. The method of claim 4 in which each subsequent development medium has an abscisic acid level lower than that of the previous development medium.

7. The method of claim 6 in which abscisic acid is reduced in stepwise fashion at each transfer to fresh development medium.

8. The method of claim 7 in which the abscisic acid concentration in each subsequent development medium is reduced to a level no greater than about 50% of the initial abscisic level in the previous development medium.

9. The method of claim 1 in which abscisic acid concentration is reduced in stepwise fashion in at least one transfer to fresh development medium.

10. The method of claim 9 in which the abscisic acid concentration in each subsequent development medium is reduced to a level no greater than about 50% of the initial abscisic level in the previous development medium at each stepwise transfer.

11. The method of claim 1 in which the abscisic acid level in the initial development medium is in the range of about 5–20 mg/L and the level in the final development medium is in the range of about 0–5 mg/L.

12. The method of claims 1, 2, or 3 in which the final development medium has an osmotic level of at least about 350 mM/kg.

13. The method of claim 12 in which at least the final and penultimate development media have osmotic levels of at least about 350 mM/kg.

14. The method of claim 13 in which the osmotic level of the final development medium is raised above the osmotic level of the penultimate medium.

15. The method of claim 1 in which the coniferous plant is *Picea abies*.

16. The method of claim 1 in which the coniferous plant is *Pinus taeda*.

17. The method of claim 1 in which the coniferous plant is *Pseudotsuga menziesii*.

18. The method of claim 12 in which the coniferous plant is *Pseudotsuga menziesii*.

* * * * *

UNITED STATES PATENT AND TRADEMARK OFFICE
CERTIFICATE OF CORRECTION

PATENT NO. : 5,236,841
DATED : August 17, 1993
INVENTOR(S) : Pramod K. Gupta and Gerald S. Pullman It is certified that error appears in the above-identified patent and that said Letters Patent is hereby corrected as shown below:

ON THE TITLE PAGE add Item 73 as follows:

[73] Assignee: Weyerhaeuser Company
Tacoma, Washington

Signed and Sealed this

Twelfth Day of August, 1997

*Attest:*

BRUCE LEHMAN

*Attesting Officer*  *Commissioner of Patents and Trademarks*